US00PP10341P

United States Patent [19]

Larsen

[11] Patent Number: Plant 10,341

[45] Date of Patent: Apr. 21, 1998

[54] OSTEOSPERMUM PLANT NAMED 'SUNNY SONJA'

[75] Inventor: Bjarne Larsen, Odense, Denmark

[73] Assignee: Paul Ecke Ranch, Encinitas, Calif.

[21] Appl. No.: 698,342

[22] Filed: Aug. 15, 1996

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Sunny Sonja', particularly characterized by its mounding growth habit with excellent dark purple spoon-shaped ray florets, mid season flowering response time, medium green foliage, and suitability to 6 inch pots, and 8 and 10 inch hanging basket cultures.

1 Drawing Sheet

BACKGROUND OF THE PLANT

The present invention relates to a new and distinct cultivar of plant known as Osteospermum. The new cultivar is known by the cultivar name 'Sunny Sonja', and was developed by the inventor Bjarne Larsen in Odense, Denmark in 1994 by crossing the cultivar designated 'Fantasy', an unpatented cultivar, with an unidentified cultivar.

Asexual reproduction by terminal (stem tip) cuttings taken by me or under my supervision at Kernen Greenhouse in Odense, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique dark purple flower color, with more consistent spoon-shaped ray flowers.

2. A mounded, compact growth habit.

3. Early flower response.

4. Well suited for 6" pots, nursery containers, and hanging baskets.

'Sunny Sonja' is similar to the cultivar 'Pink Fantasy'. The growth habit of 'Sunny Sonja' is more mounded and compact, and flowers are darker in color. Ray flowers tend to show more spoon form.

Chart A compares 'Sunny Sonja' with 'Cape Daisy Namaqua', which is described in co-pending application Ser. No. 08/695,340 which is the closest comparable plant to the knowledge of the inventor.

CHART A

| Characteristic | 'Cape Daisy Namaqua' | 'Sunny Sonja' |
|---|---|---|
| Plant Height (above the pot) | 38 cm | 38 cm |
| Plant Width | 52 cm | 67 cm |
| Flower Head Diameter | 6 cm | 6 cm |
| Color - mature ray florets | White | Purple |

DESCRIPTION OF PHOTOGRAPH

The accompanying colored photograph is a side perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif. Three rooted cuttings were transplanted into 26 cm (10 inch) hanging baskets on Dec. 11, 1995. Plants were pinched on Jan. 2, 1996, and received plant growth regulator on January 16 and 31. The values, measurements and observations noted below were taken from plants in bloom on Feb. 29, 1996 and continued flowering through April 1996.

On Apr. 10, 1996, I observed a plant in a 26 cm hanging basket 38 cm tall. This basket had three branched plants with an overall height of 53 cm and an overall width of 67 cm. Each plant had 5 strong branches, originating from within 1.5 cm of the soil line, for a total of 15 branches. Each branch was approximately 37 cm long terminating in a flower. At observation, there were 57 flowers open and 105 flower buds in various stages of development. Three secondary shoots subtend the terminal flower from the top 3 nodes on the primary shoot. These secondary shoots also terminated in a flower.

Color references are made to The Royal Horticultural Society Colour Chart (R.H.S.), except where general terms of ordinary dictionary significance are used.

THE PLANT

Origin: Seedling from cross pollination.

Parentage: Cross between seed parent 'Fantasy' and unknown pollen parent.

Classification:

*Botanical.*—*Osteospermum ecklonis.*

*Common name.*—Osteospermum.

*Cultivar name.*—'Sunny Sonja'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth.*—Standard growth retardant application for 'Sunny Sonja' includes 1–2 applications of Daminozide/butanedioic acid mono (2.2 dimethylhdrazide) at a rate of 2,500 ppm. Applications are made as foliar sprays. Growth retarding chemicals generally reduce plant height by ⅓.

Plant description:

A. *Form.*—Symmetrical, mounded perennial shrub, with good branching characteristics after pinching, giving the plant a full appearance.

B. *Habit of growth.*—Vigorous, mounding habit, producing approximately 15 leaves per stem and terminating in flowers. After the initial flowers form, typically 3 subordinate axillary shoots develop from the nodes of the uppermost leaves producing additional flowering shoots. This process is continuous so long as night temperatures remain below 16° C.

C. *Foliage description.*—1. Leaf shape: Obovate with acuminate tip and attenuate leaf base. 2. Leaf blade size: Mature leaves 8 cm long and 3.2 cm wide. 3. Petiole length: Approximately 2 cm in length. 4. Leaf margin: slightly sinuate with 3–5 pointed lobes on either side of the leaf blade. 5. Leaf texture: Slightly undulant and twisted at the tip. (i) Upper surface: Slightly pubescent with short, white trichomes evenly distributed throughout the leaf surface. (ii) Under surface: Glabrous. 6. Leaf color: Dark green. (i) Upper surface: Near R.H.S. 147A. (ii) Under surface: Between R.H.S. 146A–147B. 7. Venation: Palmately branched with light green colored mid-vein on the upper surface. One prominent mid-vein is slightly raised on the lower surface. 8. Foliage fragrance: Characteristics Osteospermum plant fragrance, particularly notable when foliage is wet.

Inflorescence description: Daisy type composite flower with disk and ray florets that close at night and open in the morning. The ligulate petal of the ray floret subtends the pistil. The disk florets contain male flower parts. Florets on the flower heads are imperfect with pistillate ray florets and staminate disk florets.

A. *Flowering habits.*—Flowering is determinate with one primary flower at the end of a long 17–20 cm pedicel on open flowers. Each pedicel had approximately 4 leaflets on the proximal end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates. Plants initially potted using rooted cuttings and pinched two weeks later, then maintained at temperatures of 10°–12° C. for four weeks and maintained for seven weeks at temperatures of about 18° C. will flower in approximately 13 weeks.

C. *Flower buds.*—Flower buds develop successively on secondary branches, reaching a size of 2 cm long and 1 cm wide prior to opening.

D. *Flowers borne.*—Singularly 9 cm above the plant canopy.

E. *Quantity of flowers.*—Secondary flowers occur progressively around the primary flower so that tight buds to mature flowers are visible at the same time.

F. *Flower head.*—1. Number of florets: 17–20 ray florets and numerous disk florets, making up a flower disk approximately 1.3 cm in diamters. 2. Shape: Narrow linear florets with obtuse to acute tips and acute bases. Ray florets approximately 2.5 cm long and 0.5 cm wide with mid-section curling to 0.1 cm wide. 3. Color: Ray florets are bright purple; disk florets are violet-blue. (i) Upper surface of ray florets: Near R.H.S. 77B and 78B. (ii) Under surface of ray florets: Near R.H.S. 83B and near 94B at the base of each floret. (iii) Disk florets: Near R.H.S. 96B. 4. Surface: (i) Upper surface of ray florets: Glaborous. (ii) Under surface of ray florets: Glaborous but pubescent near the base. 5. Flower head size: Up to 6 cm in diameter.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2 to 3 mm long and purple. 6. Ovary: Inferior to florets and green in color.

H. *Resistance.*—1. Frost resistance: Withstands light frost. 2. Diseases: Resistant to most root, stem, foliage and flower diseases.

What is claimed is:

1. A new and distinct cultivar of Osteospermum plant named 'Sunny Sonja' as illustrated and described.

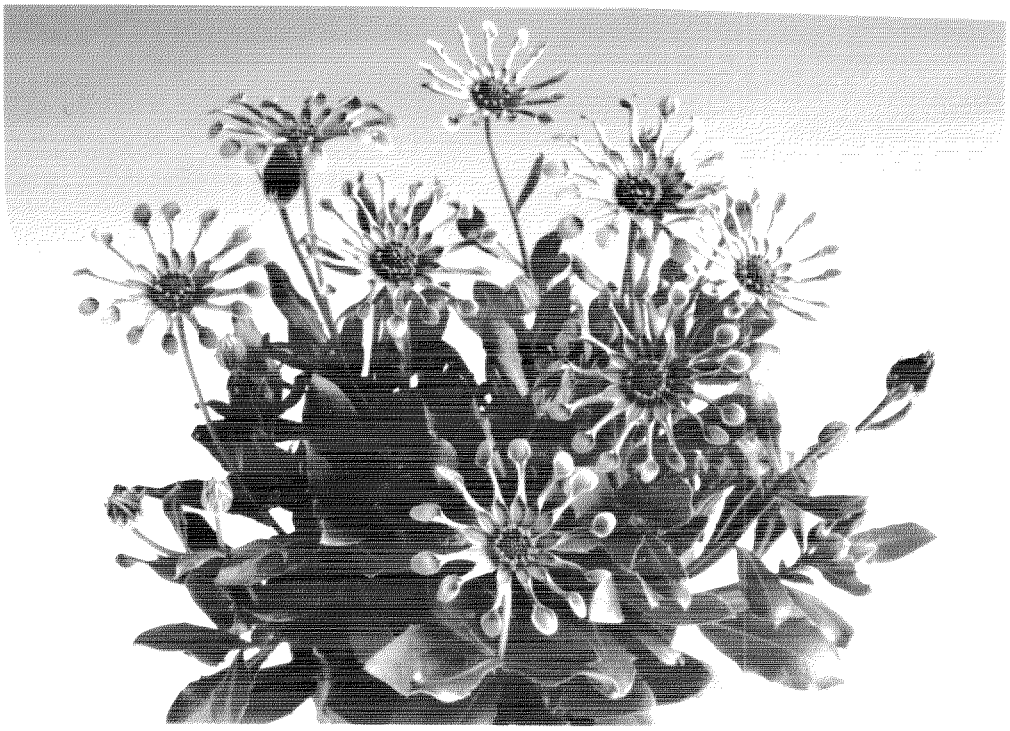

* * * * *